United States Patent
Ayres

(10) Patent No.: US 10,695,897 B2
(45) Date of Patent: Jun. 30, 2020

(54) FLUID CONTAINER DIFFUSER SYSTEM AND RELATED METHOD OF USE

(71) Applicant: DYLN INC., Irvine, CA (US)

(72) Inventor: Dorian R. Ayres, Costa Mesa, CA (US)

(73) Assignee: DYLN INC., Irvine, CA (US)

( * ) Notice: Subject to any disclaimer, the term of this patent is extended or adjusted under 35 U.S.C. 154(b) by 408 days.

(21) Appl. No.: 15/379,294

(22) Filed: Dec. 14, 2016

(65) Prior Publication Data
US 2017/0173769 A1    Jun. 22, 2017

Related U.S. Application Data

(60) Provisional application No. 62/269,534, filed on Dec. 18, 2015.

(51) Int. Cl.
| | | |
|---|---|---|
| B25B 27/02 | (2006.01) | |
| A23L 2/52 | (2006.01) | |
| B25B 13/48 | (2006.01) | |
| B25B 27/14 | (2006.01) | |
| B25B 23/00 | (2006.01) | |

(Continued)

(52) U.S. Cl.
CPC ............. B25B 27/02 (2013.01); A23L 2/52 (2013.01); A61L 9/015 (2013.01); B25B 13/481 (2013.01); B25B 23/0021 (2013.01); B25B 27/14 (2013.01); C02F 1/68 (2013.01);

(Continued)

(58) Field of Classification Search
CPC ... B25B 27/02; B25B 13/481; B25B 23/0021; B25B 27/114; B25B 3/00; B25B 23/105; B25B 27/10; B25B 27/14; A23L 2/52; A61L 9/015; A61L 2209/133; A61L 2209/134; F16L 37/248; F16L 33/22; Y10T 29/537; Y10T 29/53909; Y10T 29/53943; Y10T 29/241; Y10T 29/242; Y10T 29/278; C02F 1/68; C02F 1/688; C02F 2201/006; C02F 2307/02; C02F 1/002; B23B 51/126; B23Q 1/703; B25G 1/04; H01R 13/625; H01R 43/26; B63C 11/52; B66F 19/00; B66F 19/005; B65D 39/08; B65D 77/0486
USPC ............ 29/278, 242, 241; 81/488; 254/113; 99/317; 215/360
See application file for complete search history.

(56) References Cited

U.S. PATENT DOCUMENTS

| | | |
|---|---|---|
| 6,333 A | 4/1849 | Andrews |
| 19,960 A | 4/1858 | Van Allen |

(Continued)

FOREIGN PATENT DOCUMENTS

| | | |
|---|---|---|
| KR | 2003188810000 | 7/2003 |

OTHER PUBLICATIONS

Authorized Officer Copenheaver, Blaine, R., "International Search Report" dated Mar. 3, 2017. PCT/US2016/067029. 2 Pages.

(Continued)

*Primary Examiner* — Orlando E Aviles
*Assistant Examiner* — Robert F Neibaur
(74) *Attorney, Agent, or Firm* — Stetina Brunda Garred and Brucker

(57) ABSTRACT

A tool adapted for use with a diffuser cartridge and a fluid container, wherein the tool is adapted to facilitate insertion and removal of the diffuser cartridge to and from the fluid container. The diffuser cartridge contains mineral agent beads or other materials which can enhance the quality of fluid contained within the container.

19 Claims, 15 Drawing Sheets

(51) Int. Cl.
*C02F 1/68* (2006.01)
*A61L 9/015* (2006.01)

(52) U.S. Cl.
CPC ......... *C02F 1/688* (2013.01); *A61L 2209/133* (2013.01); *C02F 2201/006* (2013.01); *C02F 2307/02* (2013.01)

(56) References Cited

U.S. PATENT DOCUMENTS

| | | | |
|---|---|---|---|
| 65,500 A | 6/1867 | Needham | |
| 481,462 A | 8/1892 | Benson | |
| 845,717 A * | 2/1907 | Miller | B25B 13/065 139/375 |
| 1,515,247 A * | 11/1924 | Forsyth | B25B 27/023 29/264 |
| 1,736,381 A | 11/1929 | Henry | |
| 1,845,019 A | 2/1932 | Haines | |
| 2,090,320 A | 8/1937 | Amick | |
| 2,137,041 A | 11/1938 | Barnes | |
| 2,576,725 A | 11/1951 | Schoelies | |
| 2,710,109 A | 6/1955 | Amann | |
| 2,788,733 A * | 4/1957 | Jacques | A47J 31/0636 99/323 |
| 2,809,578 A | 10/1957 | Campbell | |
| 2,820,655 A | 1/1958 | Hileman | |
| 2,826,980 A | 3/1958 | Willman | |
| 2,893,331 A | 7/1959 | Medlock | |
| 2,967,776 A | 1/1961 | Utley | |
| 3,181,951 A | 5/1965 | Gronvold | |
| 3,224,940 A | 12/1965 | Ainsworth et al. | |
| 3,353,475 A | 11/1967 | Robbins | |
| 3,915,296 A | 10/1975 | Spencer et al. | |
| 4,181,071 A | 1/1980 | Outlaw | |
| 4,186,215 A | 1/1980 | Buchel | |
| 4,795,028 A | 1/1989 | Wittig et al. | |
| 4,832,968 A | 5/1989 | Forage et al. | |
| 5,031,981 A * | 7/1991 | Peterson | G02B 6/3887 385/56 |
| D327,603 S | 7/1992 | Van Asten | |
| D361,241 S | 8/1995 | Littmann | |
| 5,575,052 A * | 11/1996 | Thoresen | B25B 33/00 29/235 |
| D379,151 S | 5/1997 | Stevens | |
| 5,746,113 A | 5/1998 | Ko et al. | |
| D398,193 S | 9/1998 | Sanchez | |
| 5,913,964 A | 6/1999 | Melton et al. | |
| 6,112,537 A | 9/2000 | Broadbent et al. | |
| 6,145,685 A | 11/2000 | Dick | |
| 6,171,033 B1 | 1/2001 | Wrobel | |
| 6,431,056 B1 | 8/2002 | Fritschi | |
| 6,598,418 B2 | 7/2003 | Holley, Jr. | |
| 6,886,357 B2 | 5/2005 | Gano, III et al. | |
| 6,901,825 B1 | 6/2005 | Lebron | |
| 6,974,051 B1 | 12/2005 | Lin | |
| 7,055,706 B2 | 6/2006 | Kurs | |
| 7,096,551 B2 * | 8/2006 | Lackowski, II | B25B 27/0028 29/235 |
| D534,032 S | 12/2006 | Lloyd | |
| D592,054 S | 5/2009 | Floyd et al. | |
| D608,195 S | 1/2010 | Germann | |
| D612,235 S | 3/2010 | Cresswell et al. | |
| D614,955 S | 5/2010 | Cresswell et al. | |
| D616,743 S | 6/2010 | Cresswell et al. | |
| D616,744 S | 6/2010 | Cresswell et al. | |
| D620,357 S | 7/2010 | Jewett et al. | |
| D620,358 S | 7/2010 | Jewett et al. | |
| 7,748,657 B1 * | 7/2010 | Goodman | A01K 89/003 242/250 |
| D620,798 S | 8/2010 | Cresswell et al. | |
| D623,485 S | 9/2010 | Silvers et al. | |
| D626,416 S | 11/2010 | Cresswell et al. | |
| D630,908 S | 1/2011 | Silvers et al. | |
| 7,866,879 B2 | 1/2011 | Moschetti | |
| 7,895,939 B2 | 3/2011 | Pan | |
| D652,976 S | 1/2012 | Soto et al. | |
| D652,977 S | 1/2012 | Soto et al. | |
| 8,101,222 B2 | 1/2012 | Burroughs et al. | |
| 8,172,454 B2 | 5/2012 | Choi | |
| 8,205,542 B2 | 6/2012 | Gilbert | |
| 8,307,755 B2 | 11/2012 | Shen | |
| 8,424,448 B2 | 4/2013 | Englert et al. | |
| D695,566 S | 12/2013 | Egger et al. | |
| D703,403 S | 4/2014 | Dey et al. | |
| D703,481 S | 4/2014 | Lownds | |
| 8,720,321 B2 | 5/2014 | Neace, Jr. et al. | |
| 8,720,963 B2 | 5/2014 | Nguyen | |
| 8,757,048 B2 * | 6/2014 | Burroughs | A47G 19/2205 220/703 |
| 8,814,423 B2 * | 8/2014 | Silvers | A47G 21/023 30/164.5 |
| 8,887,625 B2 | 11/2014 | Satoh et al. | |
| 8,985,377 B2 | 3/2015 | Lane | |
| 9,120,672 B2 | 9/2015 | Satoh et al. | |
| D740,609 S | 10/2015 | Ayres | |
| 9,149,774 B2 | 10/2015 | Satoh et al. | |
| 9,314,126 B2 | 4/2016 | Molayem | |
| 9,332,873 B2 | 5/2016 | Tien | |
| D763,035 S | 8/2016 | Hume | |
| D772,014 S | 11/2016 | Ayres | |
| D811,818 S | 3/2018 | Wu | |
| D812,428 S | 3/2018 | Wu | |
| D829,058 S | 9/2018 | Seiders et al. | |
| 2004/0200232 A1 | 10/2004 | Gano | |
| 2005/0121399 A1 | 6/2005 | Hayashi et al. | |
| 2006/0162572 A1 | 7/2006 | Chiu Liu et al. | |
| 2007/0128104 A1 | 6/2007 | Hayashi et al. | |
| 2007/0221556 A1 | 9/2007 | Chung | |
| 2008/0311225 A1 | 12/2008 | Shiga | |
| 2009/0301990 A1 | 12/2009 | Cresswel et al. | |
| 2010/0000416 A1 | 1/2010 | Mulhauser | |
| 2011/0062043 A1 | 3/2011 | Bougoulas et al. | |
| 2011/0233119 A1 * | 9/2011 | Nelson | B05B 11/3001 210/117 |
| 2012/0087990 A1 | 4/2012 | Shiga | |
| 2012/0234789 A1 | 9/2012 | Mason | |
| 2013/0098250 A1 | 4/2013 | Satoh | |
| 2013/0206717 A1 | 8/2013 | Lane | |
| 2013/0239821 A1 | 9/2013 | Boettcher | |
| 2013/0305506 A1 * | 11/2013 | Mouch | B25G 1/04 29/242 |
| 2014/0044837 A1 | 2/2014 | Weisman et al. | |
| 2014/0084610 A1 | 3/2014 | Nguyen | |
| 2014/0251153 A1 | 9/2014 | Tien | |
| 2014/0326143 A1 | 11/2014 | McCrea | |
| 2014/0367318 A1 | 12/2014 | Ayres et al. | |
| 2015/0208849 A1 | 7/2015 | Melzer et al. | |
| 2015/0208853 A1 | 7/2015 | Melzer et al. | |
| 2016/0120355 A1 | 5/2016 | Shen | |

OTHER PUBLICATIONS

Authorized Officer Copenheaver, Blaine, R., "Written Opinion of the International Searching Authority" dated Mar. 3, 2017. PCT/US2016/067029. 5 Pages.

Holsworth, Ralph E., Jr., D.O., "Essesntia Alkaline & Electrolyte Enhanced Premium Water for Hydration: Technical Information", Essentia, vol. 1 Issue 1, Aug. 1999, Copyright 1999 Essentia Water, 7 pages.

* cited by examiner

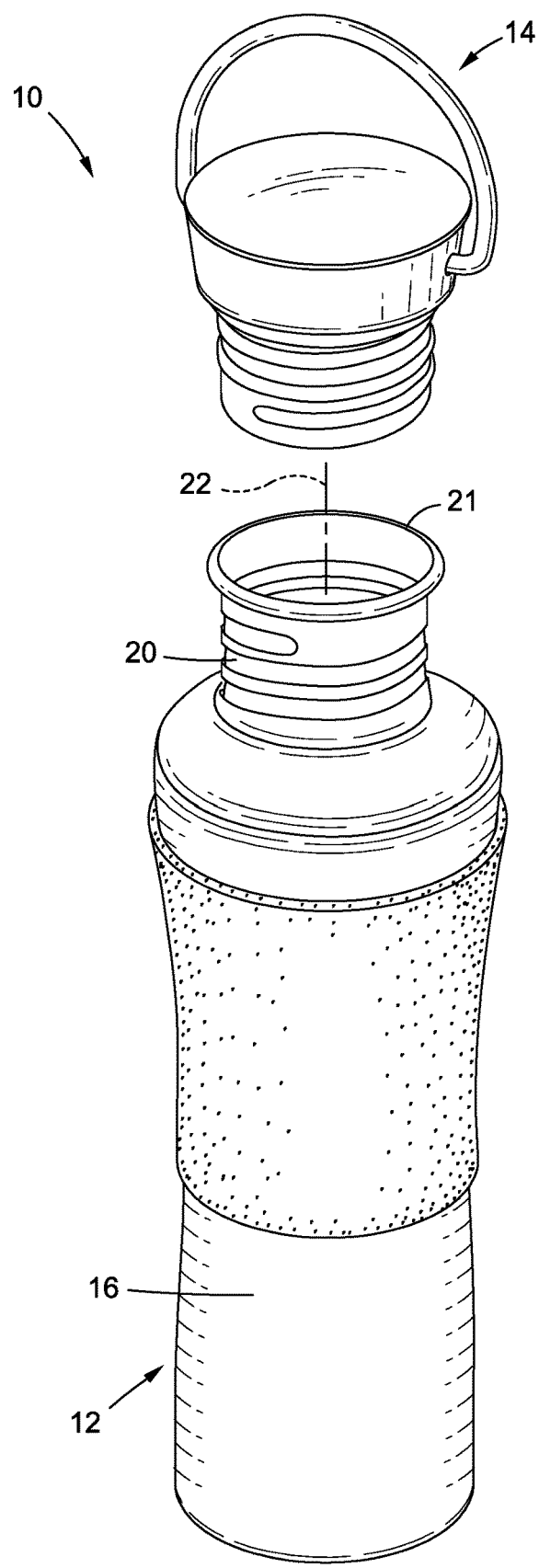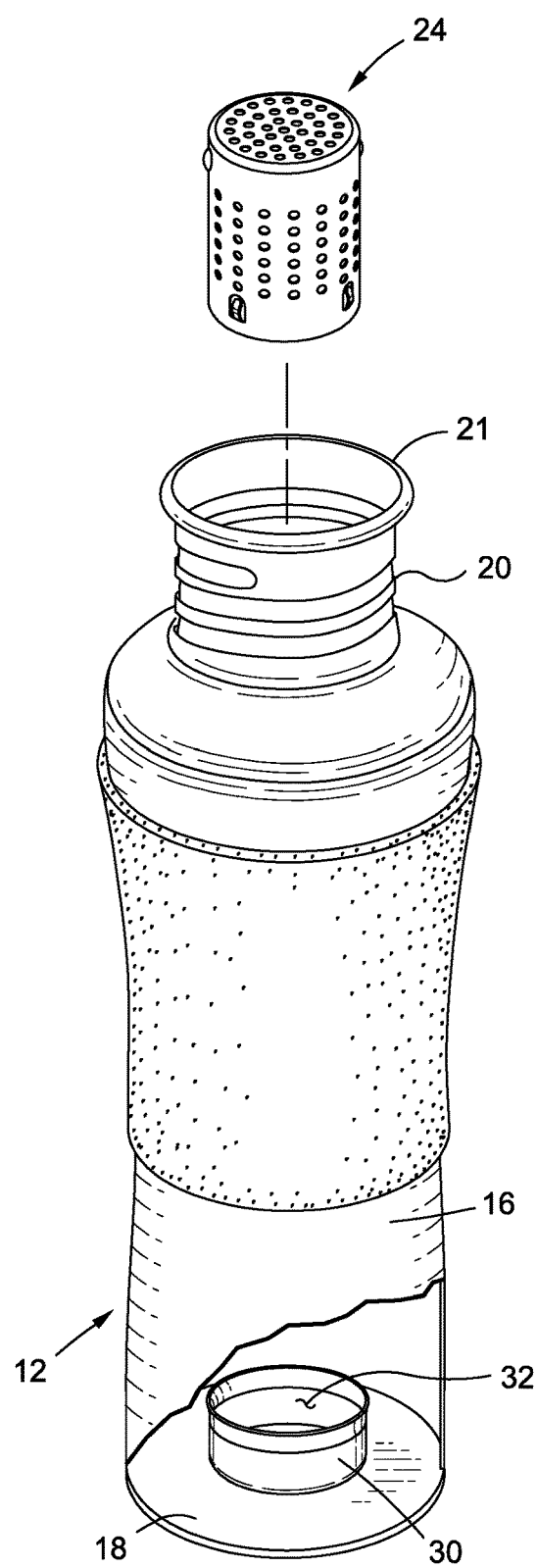
FIG. 1  FIG. 2

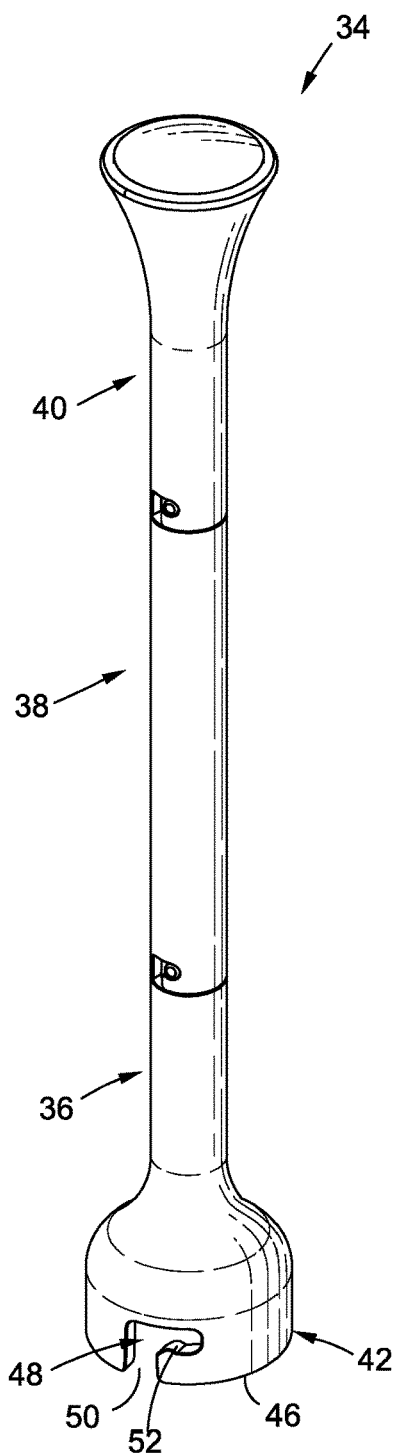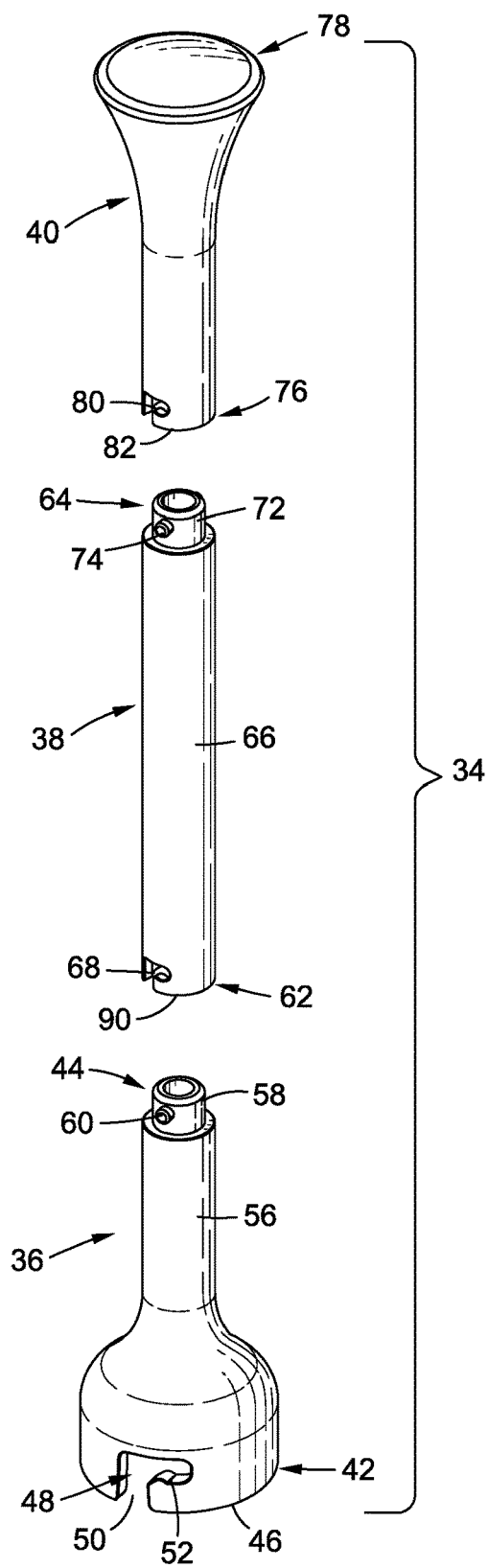
FIG. 6
FIG. 7

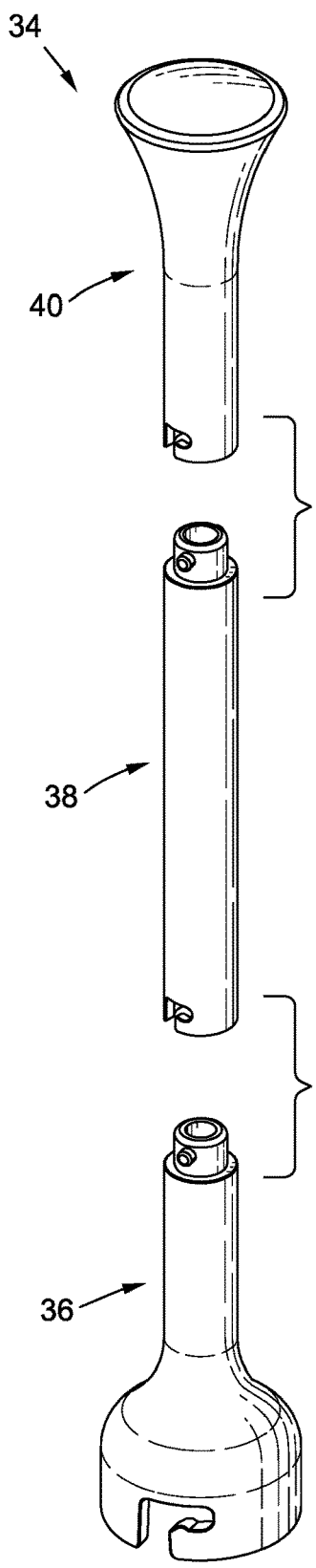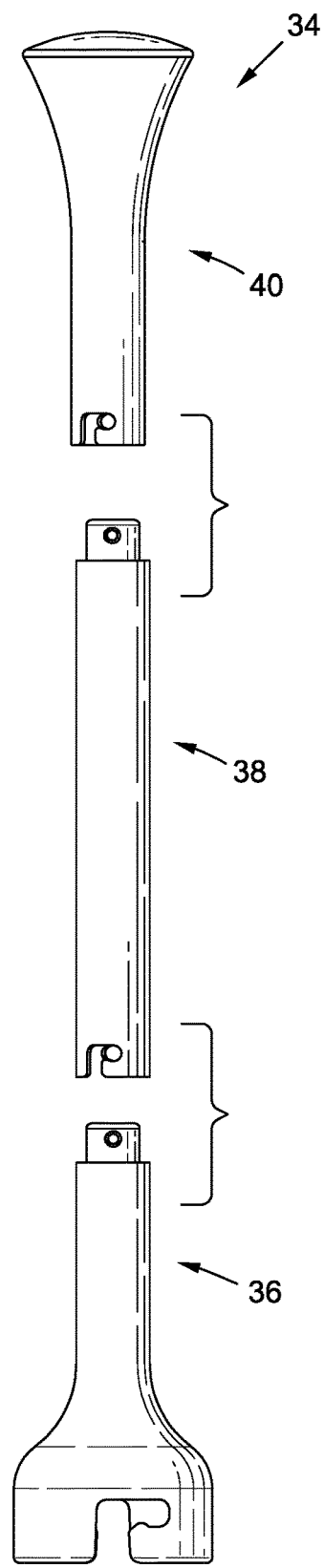
FIG. 12              FIG. 13

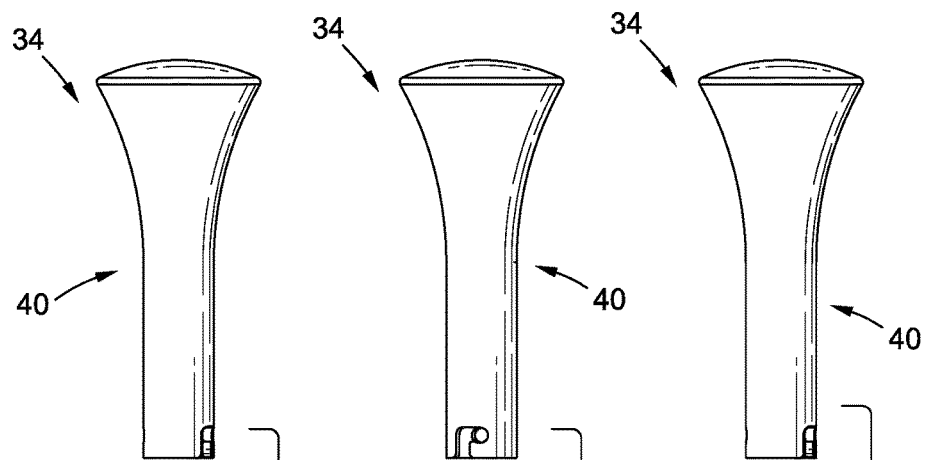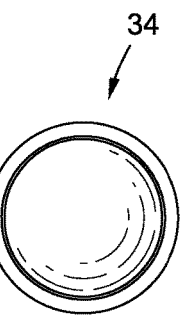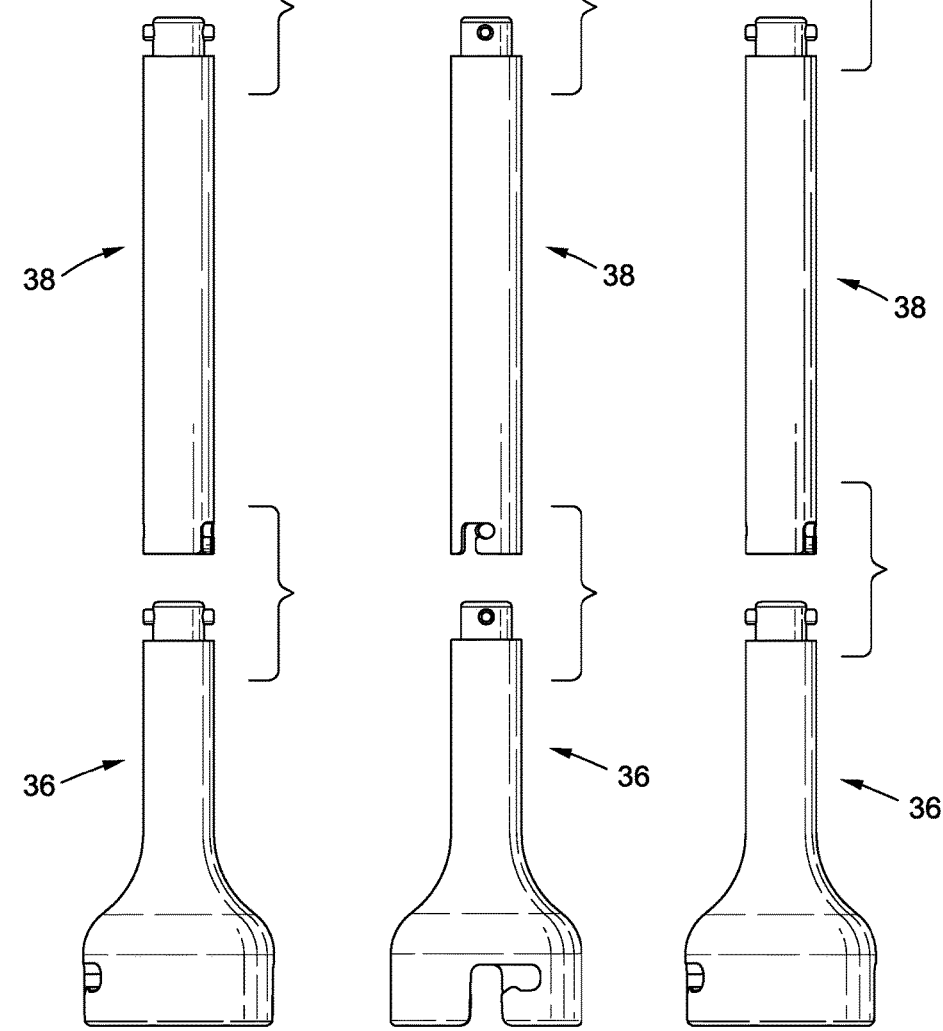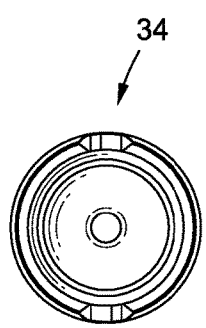
FIG. 14  FIG. 15  FIG. 16

FLUID CONTAINER DIFFUSER SYSTEM AND RELATED METHOD OF USE

CROSS-REFERENCE TO RELATED APPLICATIONS

This application claims the benefit of U.S. Provisional Application No. 62/269,534, filed Dec. 18, 2015, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to an extension tool, and more specifically, to an elongate tool adapted to facilitate insertion of a diffuser cartridge into a water bottle.

2. Description of the Related Art

Personal hydration includes the need for portable drinking fluid containers and bottles. Because of the sustainability and environmental issues associated with plastic and single use water bottles, consumers are attracted to reusable containers as such as stainless steel water bottles. Also stainless steel bottles can be formed to be free of BPA, lead or other toxins making for a healthier container. In addition, consumers have recognized the health benefits of treated drinking fluids such as alkaline water. In this regard, there is a need in the art for combining the benefits of reusable containers in combination with the easy availability of treated fluids such as alkaline water.

Alkaline water is understood to be beneficial to health for maintaining physical stability and helping to deal with acid buildup in the body in both healthy individuals and those with conditions that cause acidification of the blood. Alkaline water is said to aid in digestion, neutralize acidity, and to also assist in reducing free radicals. In addition, in most instances, alkaline water has the characteristic of smaller water clusters, and a pH above 7.0 that has also been identified as allowing the body to more easily absorb the water. Generally, alkaline water is obtained by water electrolysis and/or through chemical treatment by mineral agents. In many prior art devices for creating alkaline water, electricity is used in association with an apparatus, or otherwise such devices have complex structures that are not conducive for treating drinkable fluids in a portable manner. A discussion of the types and systems for creating alkaline water are described in Chung, U.S. Publication No. 2007/0221556, published Sep. 27, 2007, the substance of which is incorporated herein by reference.

Prior art devices also disclose the use of mineral agents in fluid vessels, to allow untreated water to come in contact with the agents to form alkaline water. Such prior art devices however include multi-part structures that are not user friendly and may not remain fixed in a vessel, as intended, or otherwise use an undesirable amount of volume within a vessel and do not facilitate the flow of water around the mineral agents. As such there is a need in the art for the worry free use of a reactive agent in a portable fluid vessel, that will not overtake the functional use of the vessel and use an undesirable amount of volume of the bottle.

Furthermore, many fluid vessels are shaped to include a closed end portion and an open end portion formed at a narrow neck of the fluid vessel. The narrow configuration of the fluid vessel may make it difficult to insert the structures associated with the mineral agents into the fluid vessel. Thus, there is also a need in the art for a device which facilitates insertion of the mineral agents into the fluid vessel.

Various aspects of the present disclosure address this particular need, as will be discussed in more detail below.

BRIEF SUMMARY

In accordance with one embodiment of the present disclosure, there is provided a tool adapted for use with a diffuser cartridge and a fluid container, wherein the tool is adapted to facilitate insertion and removal of the diffuser cartridge to and from the fluid container. The diffuser cartridge contains mineral agent beads or other materials which can enhance the quality of fluid contained within the container.

According to one embodiment, the tool is adapted for use with the diffuser cartridge and a fluid containment vessel having a base, a retaining wall coupled to the base, and an upper rim, with the base and upper rim defining a vessel height. The diffuser cartridge is detachably engageable with the retaining wall to assume a nested configuration. The tool includes a bottom segment having a first end portion complimentary in shape to the diffuser cartridge and adapted to be selectively engageable with the diffuser cartridge, and a second end portion having a bottom segment connector. The tool further includes an intermediate segment separate from the bottom segment and having a first intermediate connector adapted to engage with the bottom segment connector, and a second intermediate connector. The tool additionally comprises a top segment separate from the bottom segment and intermediate segment, with the top segment having a top segment connector adapted to engage with the second intermediate connector. The intermediate segment is connected to the bottom segment and the top segment when the tool is in an assembled configuration, with the tool being sized and configured such that an end surface of the diffuser cartridge and a portion of the top segment of the tool collectively define an operating length greater than the vessel height.

The bottom segment may include a cavity adapted to receive a portion of the diffuser cartridge when the first end portion of the bottom segment is engaged with the diffuser cartridge. The bottom segment may also include a channel adapted to receive a portion of the diffuser cartridge to effectuate engagement between the bottom segment and the diffuser cartridge. The channel may include an axial segment and a radial segment.

The top segment may include an enlarged end portion opposite the top segment connector, with the enlarged end portion being sized and configured to be grippable by the user.

The tool may be sized and configured to extend from the diffuser cartridge and beyond the upper rim of the fluid containment vessel when the first end portion is engaged with the diffuser cartridge.

The bottom segment, intermediate segment and top segment may be formed from a plastic material. The intermediate segment and portions of the top and bottom segments may each define an outer diameter substantially equal to each other.

The tool may be formed of a plurality of interconnectable elements, which when connected, define a length that is long enough to allow the user to insert or remove the diffuser cartridge from the fluid container while the user's hand remains outside of the container. As such, the user is not required to squeeze his or her hand through the narrowing opening commonly associated with such fluid containers. The tool and the use thereof allows for the attachment of the diffuser to the bottom of the vessel without the need to have a mechanism for accessing or opening the bottom of the vessel. Adapting a fluid vessel to have a bottom opening increases cost of manufacture and increases the complexity of use, among other issues. Also, having the diffuser located at the bottom of the vessel aids in increasing the amount of contact of diffuser ingredients will have with the liquid, as opposed to situating the diffuser in the container lid, for example, where liquid may not contact a diffuser when the container is less than completely full.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 1 is an upper perspective view of a container including a vessel body and a cap;

FIG. 2 is an upper perspective, partial cutaway, exploded view of a diffuser cartridge adapted to be nested within a retaining wall located within the vessel body;

FIG. 6 is an upper perspective, assembled view of a tool adapted for insertion and removal of the diffuser cartridge to and from the vessel;

FIG. 7 is an upper perspective, exploded view of the tool shown in FIG. 6;

FIGS. 12-23 show various views of one particular embodiment of the tool.

Common reference numerals are used throughout the drawings and the detailed description to indicate the same elements.

DETAILED DESCRIPTION

The detailed description set forth below in connection with the appended drawings is intended as a description of certain embodiments of a tool for inserting a diffuser cartridge into a fluid containment vessel, such as a water bottle, and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Figure 8:
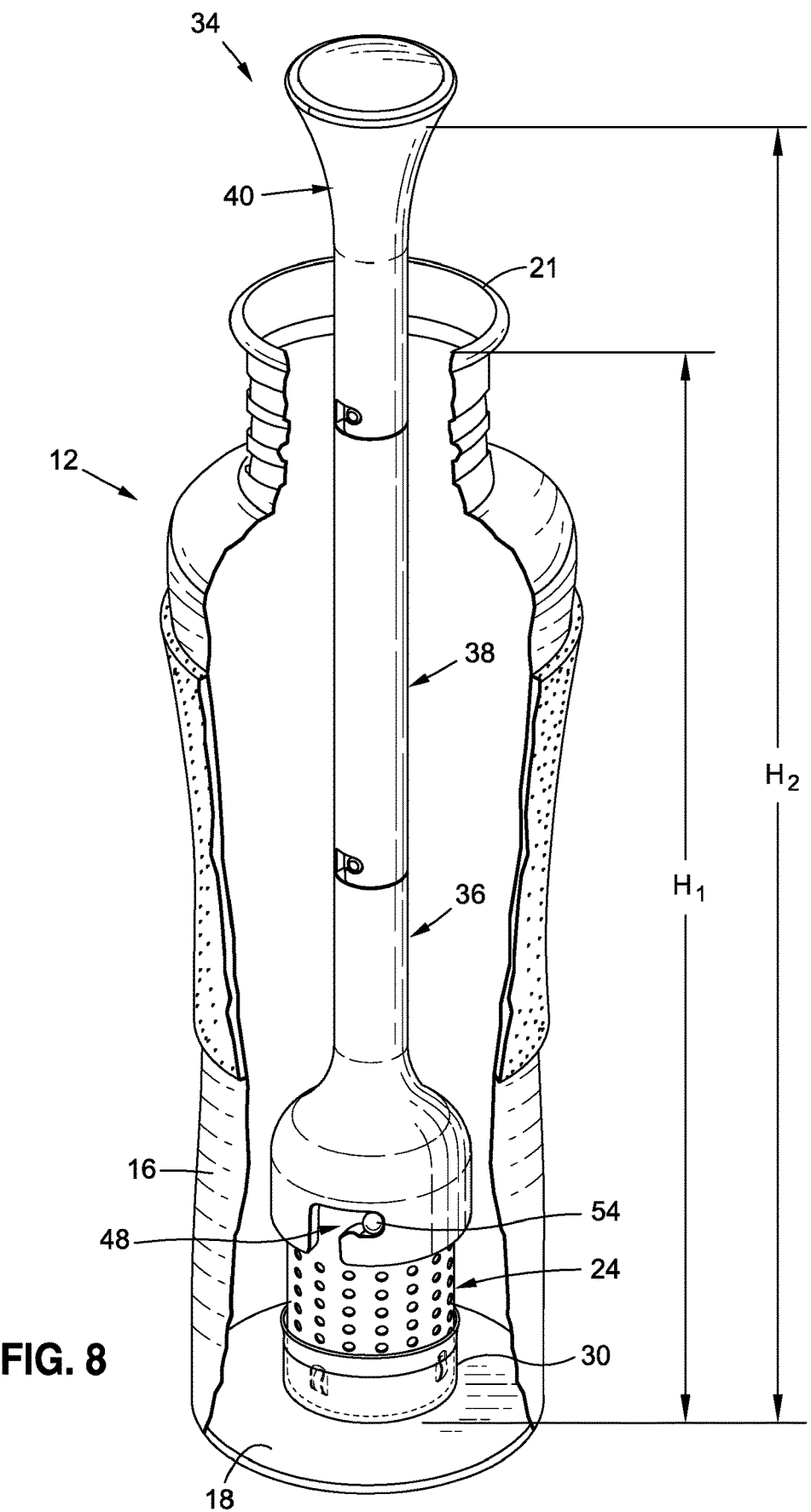
FIG. 8 is an upper perspective, partial cutaway view showing the tool engaged with the diffuser cartridge, with the diffuser cartridge being engaged with the vessel body.
Figure 9:
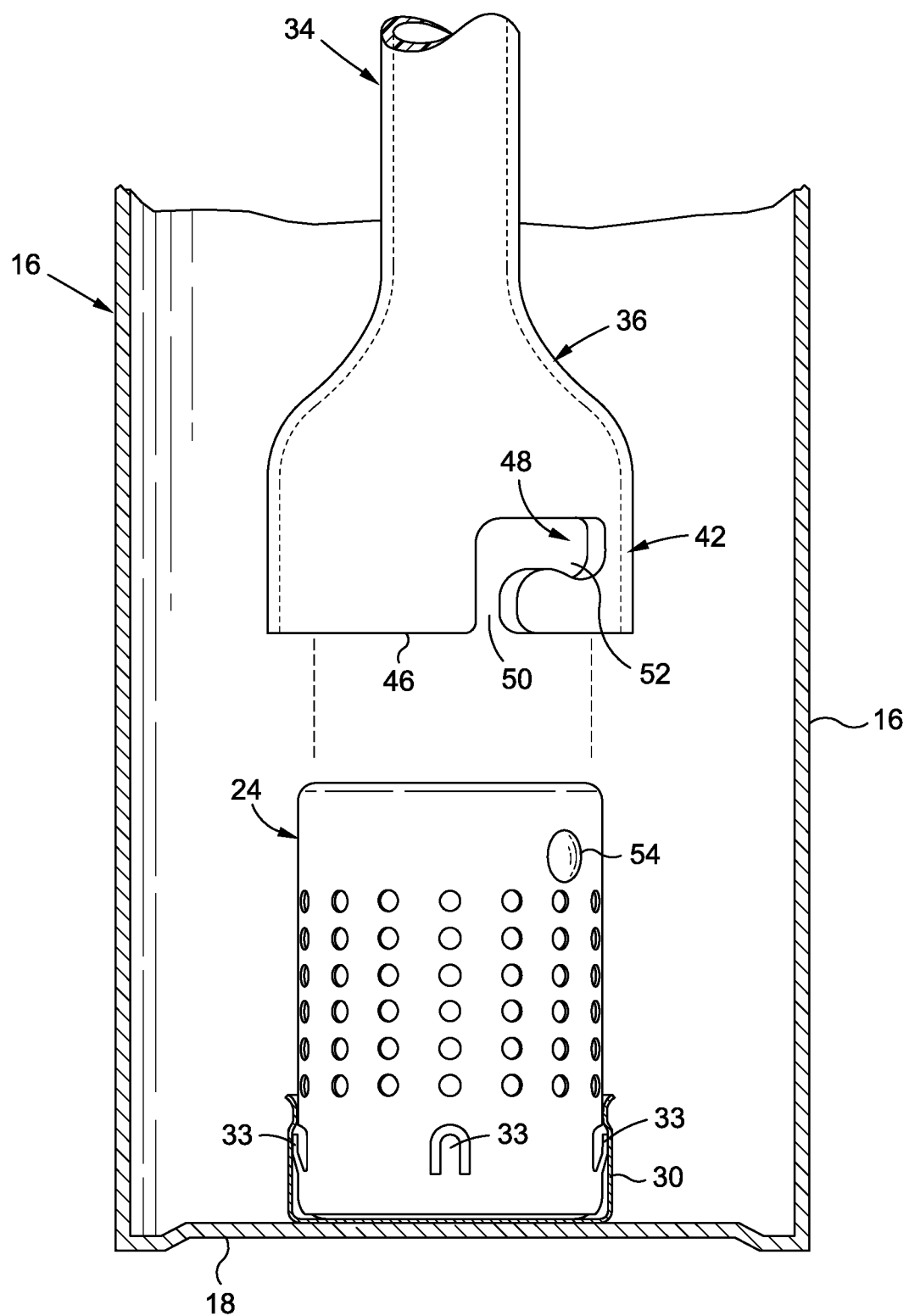
FIGS. 9-11 show a sequence of connecting the tool to the diffuser cartridge, and removing the diffuser cartridge from the vessel using the tool.
Figure 10:
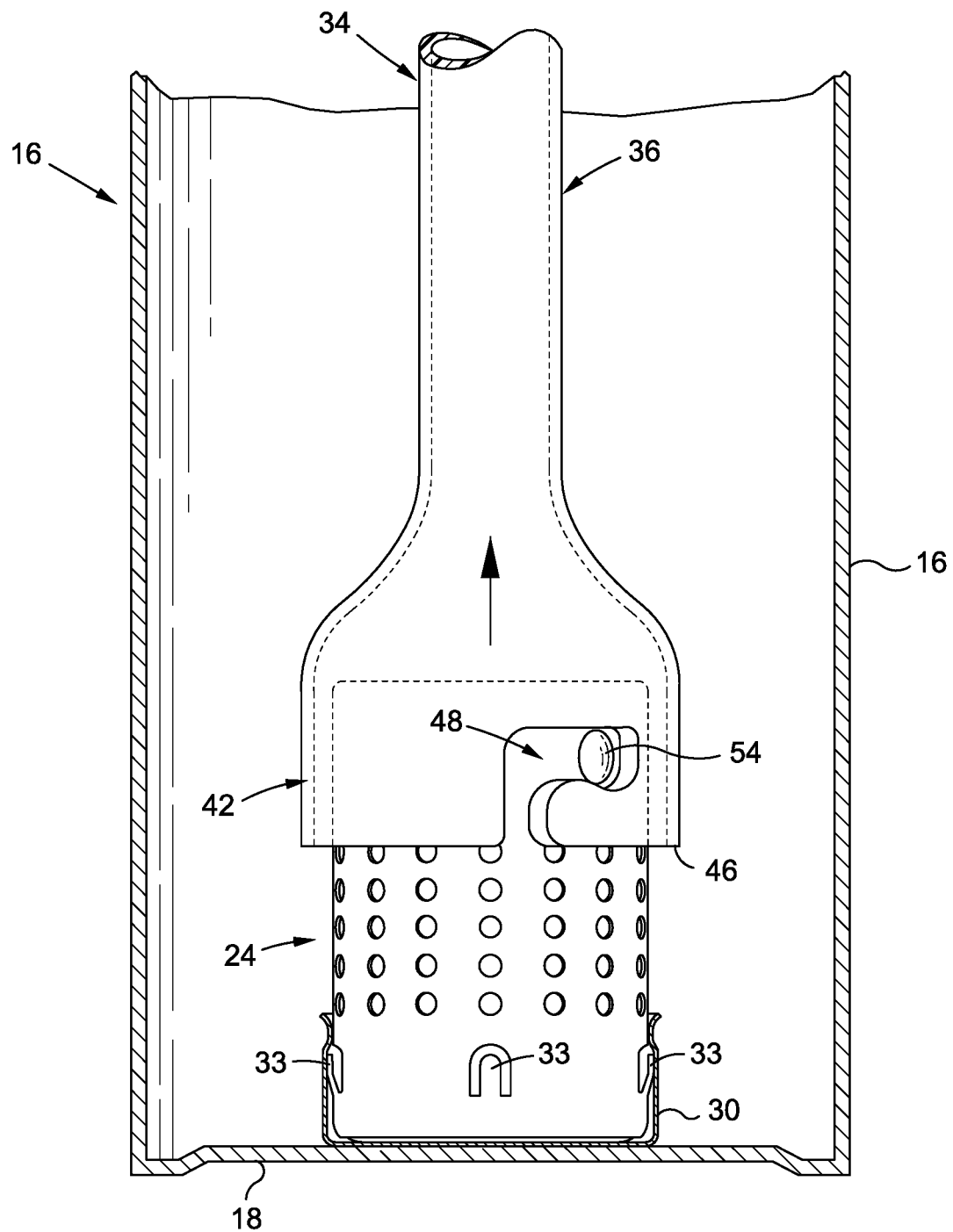
Figure 11:
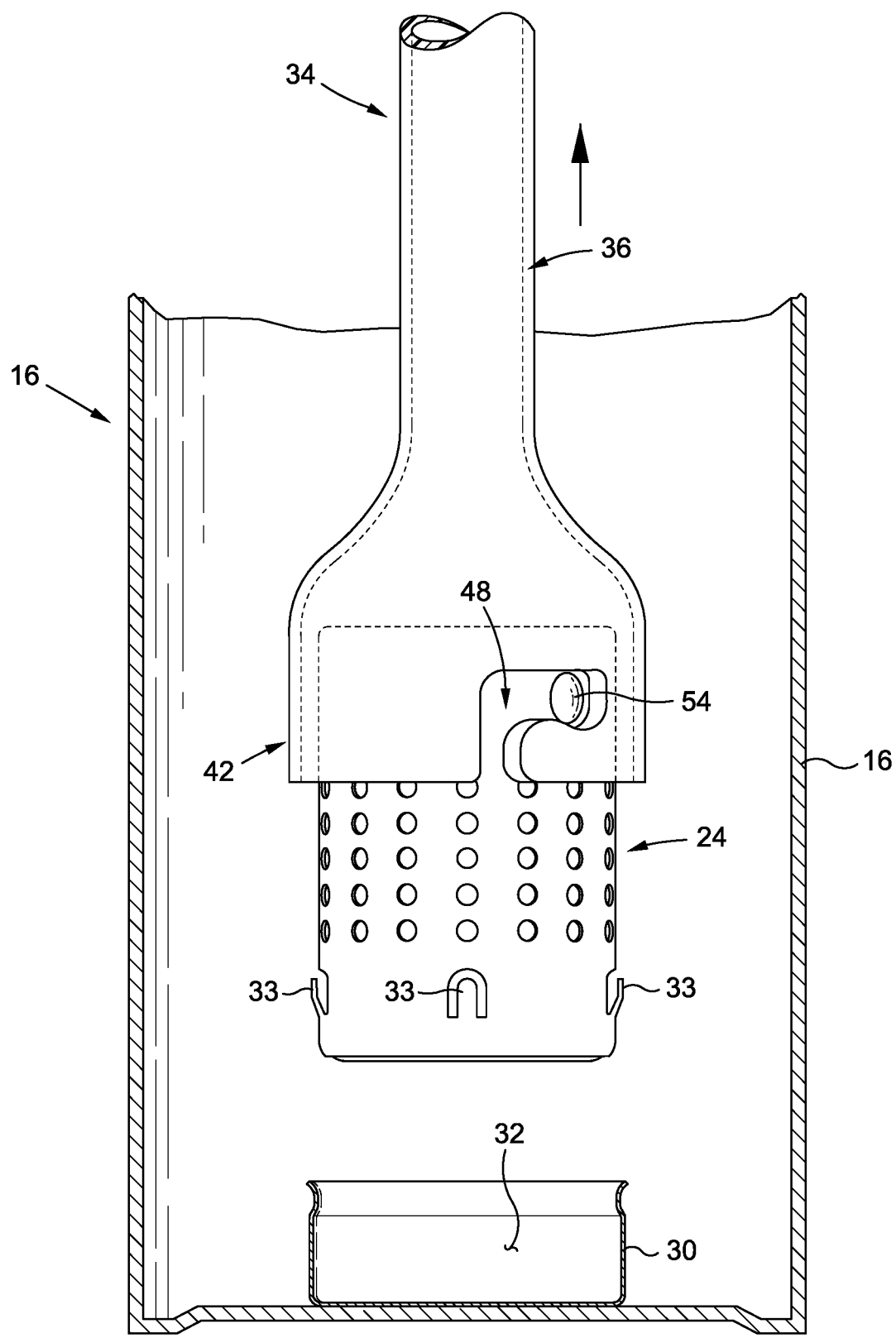
Figures 19, 20:
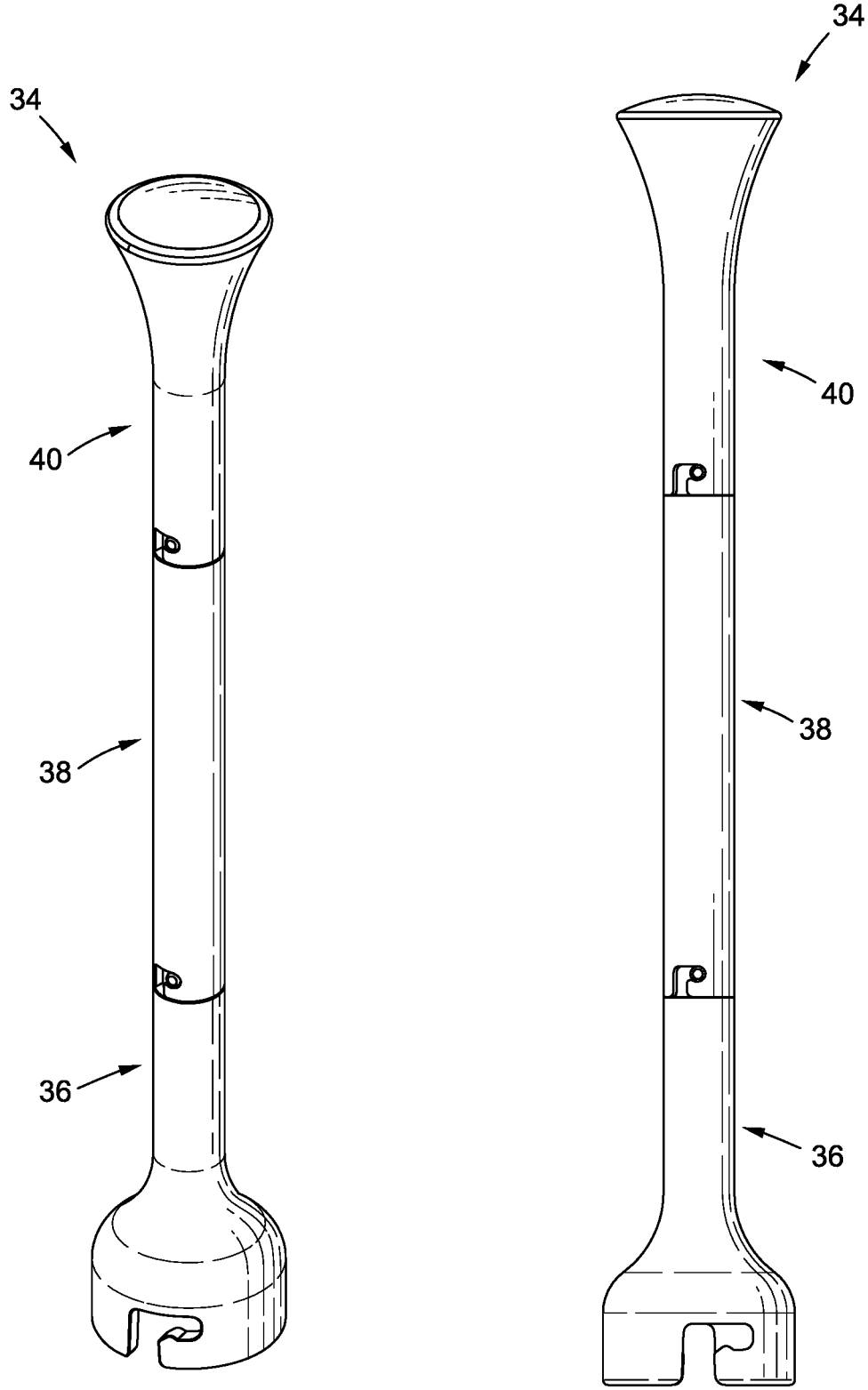
Figure 21:
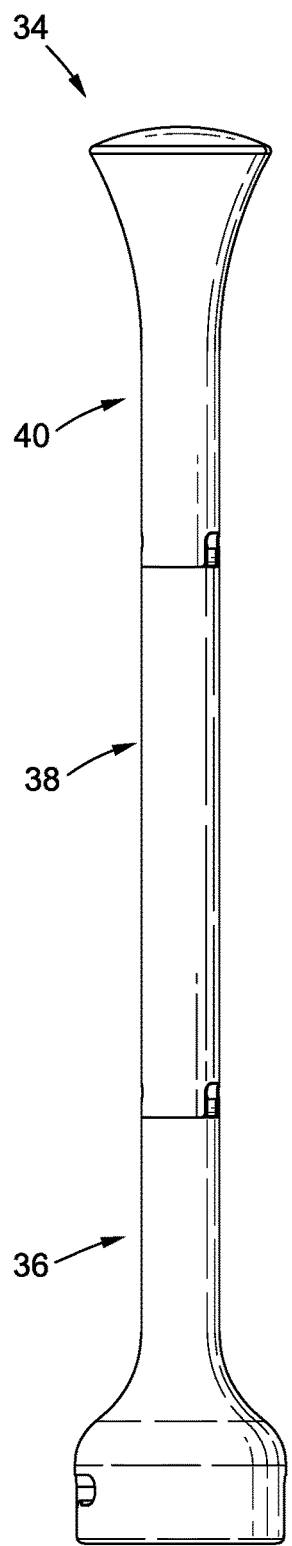
Figure 22:
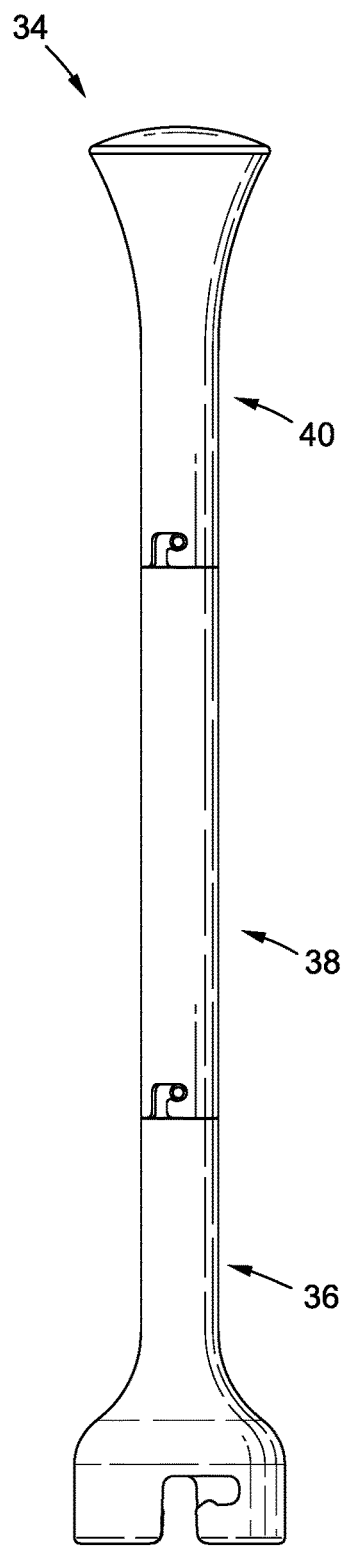
Figure 23:
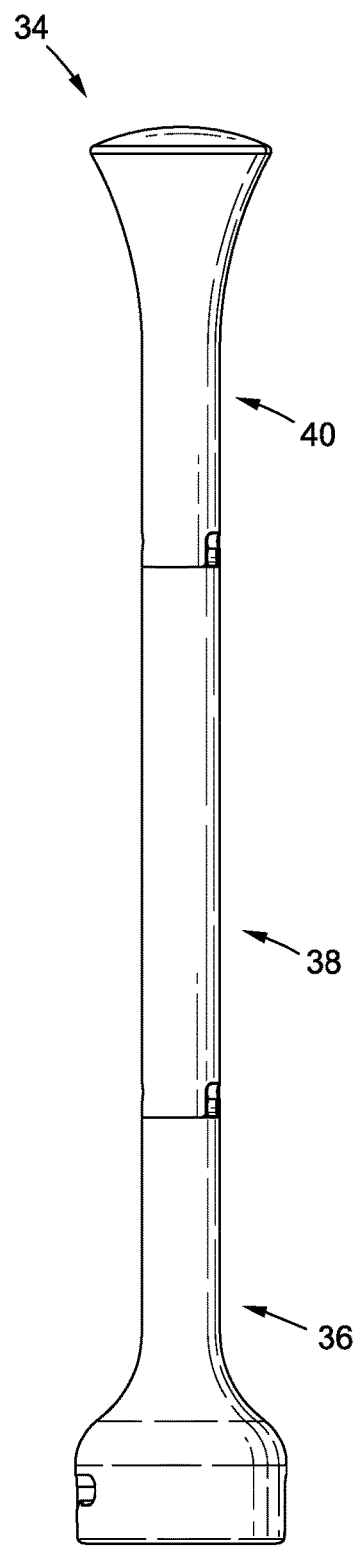

Referring now to FIGS. 1-5, there is shown a fluid containment vessel (e.g., container) 10 including a vessel body 12 and a cap 14 operatively engageable with the vessel body 12. The vessel body 12 is formed from an elongate stainless steel sidewall 16 and a base 18, with the sidewall 18 being tapered at a neck portion 20 adapted to interface with the cap 14. The neck portion 20 terminates at an upper rim 21, with the vessel body 12 having a first height $H_1$ (see FIG. 8) equal to the distance between the base 18 and the upper rim 21. A user can selectively open and close the container 10 by securing the cap 14 to the vessel body 12 at the neck portion 20. An o-ring may be employed on the cap 14 to assist in forming a fluid tight seal when the cap 14 is placed on the vessel body 14 to close the container 10.

The sidewall 16 is disposed about a central axis 22, with the neck portion 20 providing an opening for which fluid can be inserted or extracted from the vessel body 12 and is wide enough to promote drinking directly from the vessel body 12. A portion of the sidewall 16 may be covered by a gripping pad to enhance the grippability thereof. It is contemplated that the sidewall 16 may be a single wall or a double wall, with the double wall configuration being employed to enhance the insulating characteristics of the vessel body 12. Along these lines, an insulating material or substance may be disposed between the double walls.

A diffuser cartridge 24 is detachably affixable/engageable to the base 18 and is adapted to having mineral agent beads 26 (see FIG. 5) or other materials that can interact with and treat a fluid contained within the vessel body 12. The mineral agent beads 26 are secured within the cartridge 24 so as not to escape from the cartridge 24 and into the void of the vessel body 12. The exemplary cartridge 24 is of a cylindrical shape, although those skilled in the art will readily appreciate that the cartridge 24 may take on other shapes including, but not limited to a spherical shape, a cuboid shape, or any other shapes.

The cartridge 24 includes a plurality of perforations 28 formed therein, with the perforations 28 being sized relative to the mineral beads 26 so as to retain the mineral beads 26 within the cartridge 24, while at the same time allowing the beads 26 to be bathed within the water/fluid contained within the vessel body 12. The perforations 28 shown in the drawings are arranged in rows and columns, although the perforations 28 may be formed on the cartridge 24 in any arrangement or pattern. The cartridge 24 depicted in the Figures is a two-part assembly, with an upper body 25 and a lower body 27 that engages with the upper body 25. The two-part construction of the cartridge 24 facilitates insertion of the filtering beads 26 during manufacture of the cartridge 24. The lower body 27 includes an end wall having the perforations formed therein, and an annular wall extending from the end wall and engaging with the upper body 25. The upper body 25 include an open end portion which receives the lower body 27, with the upper body 25 having a slightly reduced diameter adjacent the open end portion so as to engage with and retain the lower body 27. The perforations 28 formed on the exemplary cartridge are formed in both the upper and lower bodies 25, 27. According to one embodiment, the cartridge 24 defines an outer diameter preferably between 0.5-2.0 inches, and more preferably equal to approximately 1.125 inches. Furthermore, the height of the cartridge 24 is preferably between 1.0-3.0 inches, and more preferably equal to approximately 1.6875 inches.

The cartridge 24 is adapted to engage with a retaining wall 30, which extends around a retaining cavity 32 and is coupled to the base 18 of the container 10. The retaining wall 30 and corresponding retaining cavity 32 are complimentary in shape to the cartridge 24 to allow the cartridge 24 to be selectively nested within the retaining cavity 32 and engaged with the retaining wall 30 to affix the cartridge 24 to the vessel body 12. The cartridge 24 and the retaining wall 30 are configured to become sufficiently engaged with each other when the cartridge 24 is nested within the retaining cavity 32 so as to hold the cartridge 24 in the nested position as the user repeatedly tips the vessel body 12 to drink the water contained therein. In this regard, the cartridge 24 and the retaining wall 30 may be adapted to create such engagement via a friction-tight fit, spring-type tabs 33, locking rims, etc.

Figure 3:
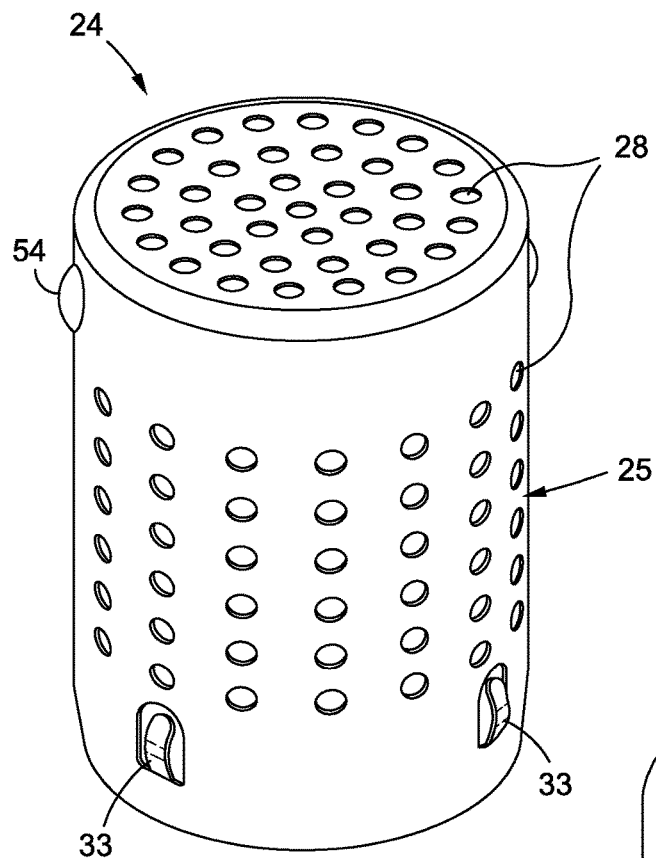
FIG. 3 is an upper perspective view of the diffuser cartridge.
Figure 4:
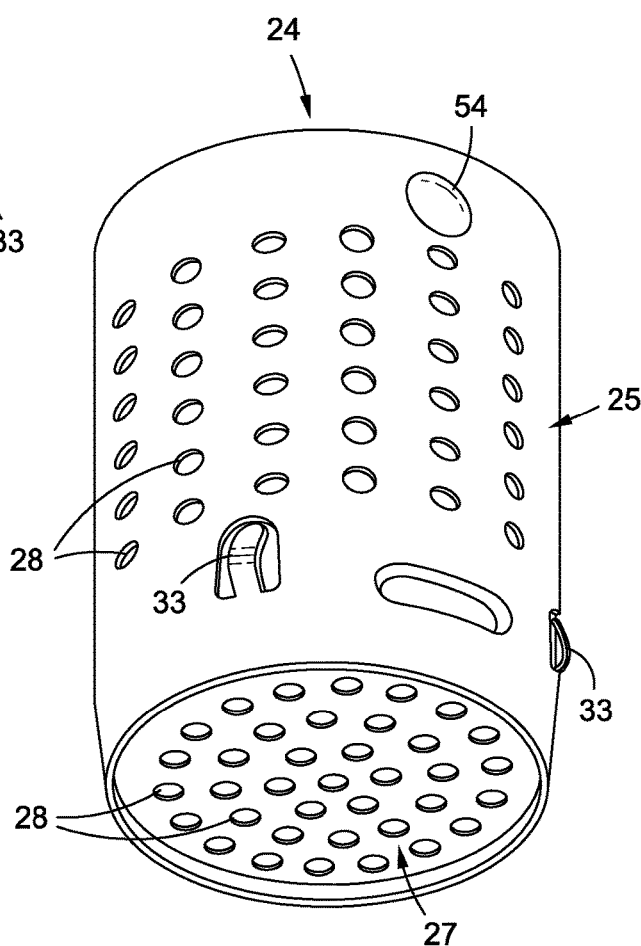
FIG. 4 is a lower perspective view of the diffuser cartridge.
Figure 5:
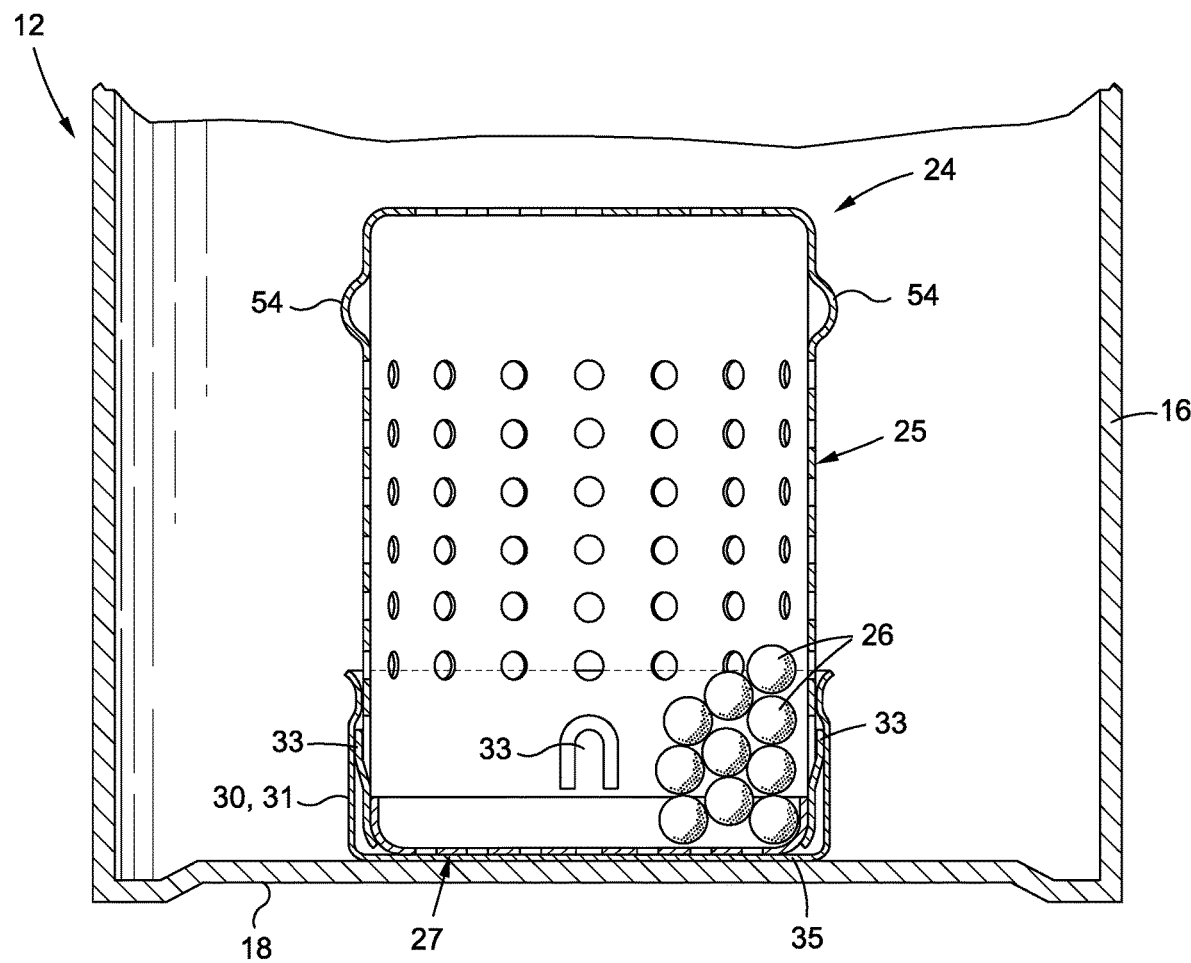
FIG. 5 is a front cross sectional view of a bottom portion of the vessel body, with the diffuser cartridge being nested within the retaining wall, a portion of the diffuser cartridge being cutaway to reveal mineral beads within the diffuser cartridge.

FIG. 5 is a cross sectional view of a lower portion of the container 10 showing the cartridge 24 engaged with the raining wall 30. In the embodiment depicted in FIG. 5, the retaining wall 30 includes an annular portion 31 and a bottom plate 35, with the annular portion 31 extending upwardly from the bottom plate 35. The bottom plate 35 is connected to the base 18 of the vessel body 12 in direct flat-to-flat engagement. That is to say, a bottom planar surface of the bottom plate 35 is placed in opposed relation to a planar surface of the base 18. The bottom plate 35 may be attached to the base 18 via welding, an adhesive, or other mechanical joining techniques known by those skilled in the art.

Figure 5A:
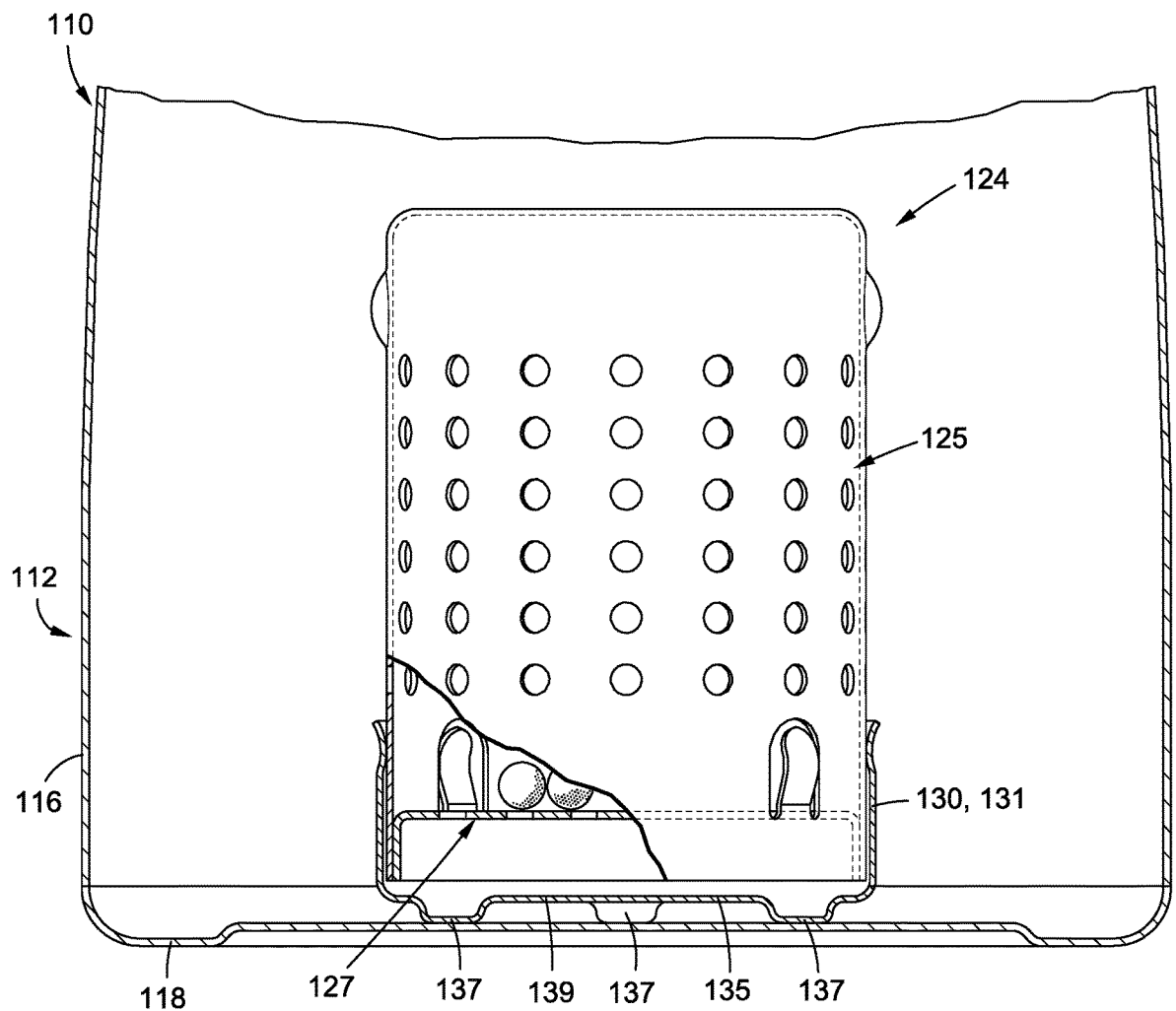
FIG. 5A is a front cross sectional view of another embodiment of a bottom portion of the vessel body, and a diffuser cartridge, with the diffuser cartridge being nested within a retaining wall.
Figure 5B:
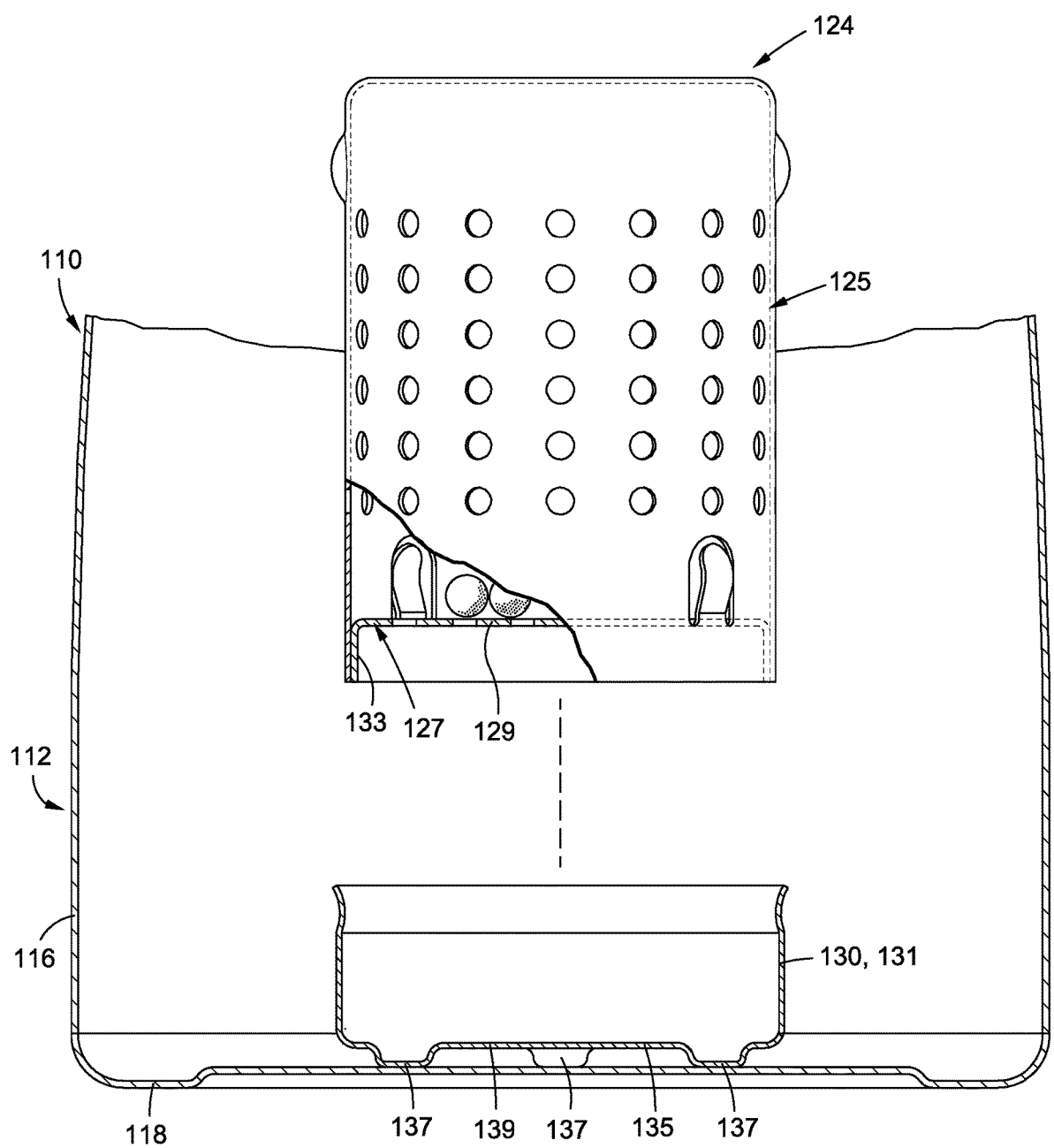
FIGS. 5B and 5C are partial and completely exploded views, respectively, of the embodiment depicted in FIG. 5A.
Figure 5C:
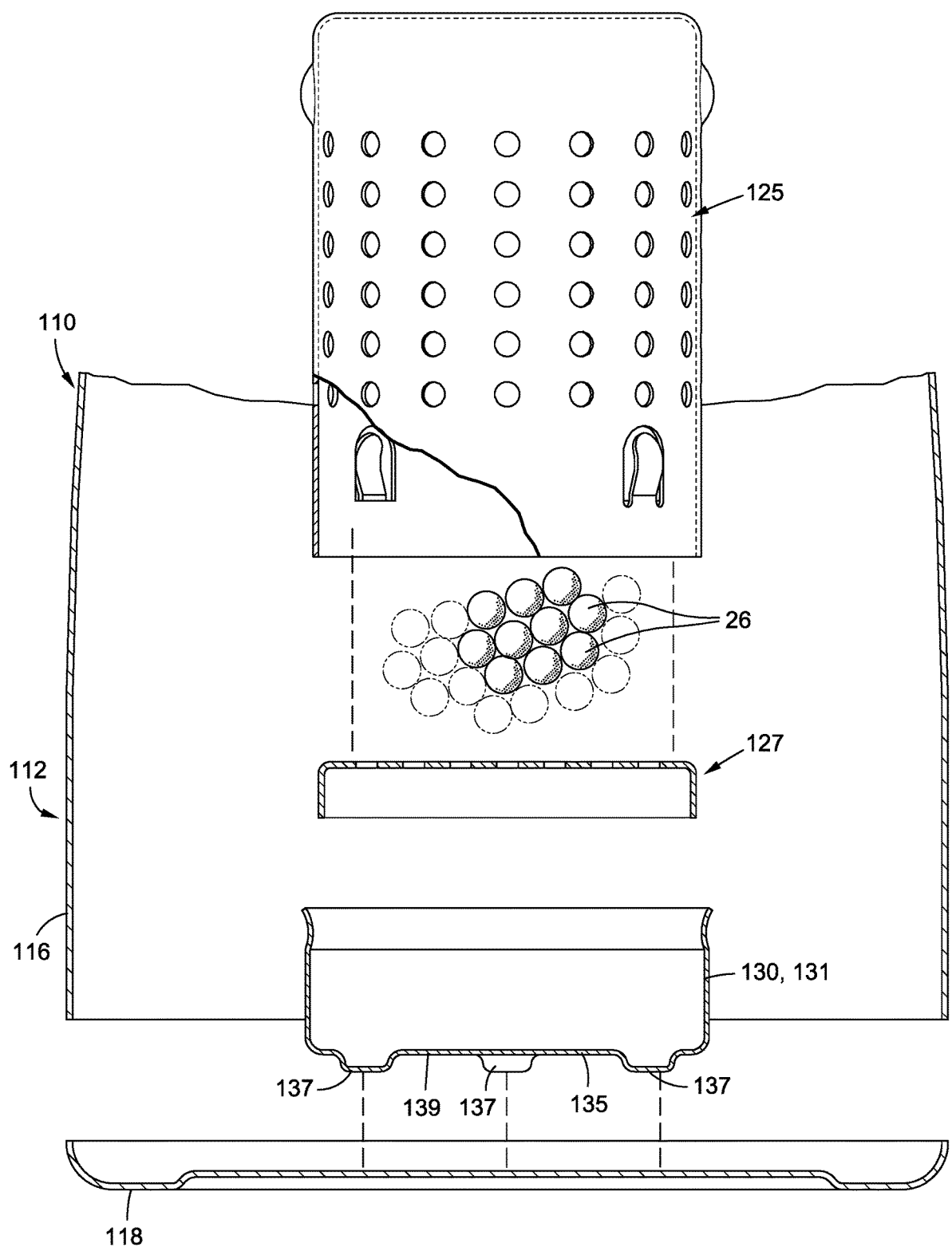

Referring now to FIGS. 5A-5C, there is depicted an alternative embodiment of the lower portion of the container 110. A vessel body 112 is shown having a base 118 which differs slightly from the base 18 shown in FIG. 5. In particular, the base 118 includes rounded transition with sidewall 116, whereas in the embodiment depicted in FIG. 5, the transition between the base 18 and sidewall 16 is square.

The container 110 further includes a retaining wall 130 including an annular portion 131 and a bottom section 135. The bottom section 135 includes a plurality of nubs or protuberances 137 extending from a bottom plate 139, with the nubs/protuberances 137 providing a structure to which the base 118 may be spot welded or otherwise coupled. In this regard, the entire bottom section 135 is not in flat-to-flat engagement with the base 118, and in fact, the bottom plate 139 may be spaced from the base 118 when the nubs/protuberances 137 are coupled to the base 118.

The container 110 further includes cartridge 124 which slightly differs from cartridge 24 discussed above. In particular, cartridge 124 includes an upper body 125 and a lower body 127. The primary distinction between the cartridge 124 shown in FIGS. 5A-C relative to the cartridge 24 shown in FIG. 5 is that the lower body 127 is inverted relative to the lower body 27. In particular, the lower body 127 includes an end wall 129 that is located within the upper body 125, with the lower body 127 including an annular wall 133 extending from the end wall 129 toward a terminal edge of the upper body 125 adjacent the open end portion of the upper body 125 when the lower body 127 is engaged with the upper body 125. Such engagement between the upper and lower bodies 125, 127 may be facilitated through press-fit engagement, or through the use of other mechanical fastening mechanisms, including but not limited to adhesives, fasteners or the like.

For more information pertaining to a structure of a vessel body and diffuser cartridge, please refer to United States Patent Application Publication No. 2014/0367318, entitled Fluid Container with Internal Perforated Compartment, the contents of which are expressly incorporated herein by reference. The following discussion will focus on the structure and use of a specifically configured tool 34, as shown in FIGS. 6-23, for inserting the diffuser cartridge 24 into the vessel body 12, and subsequently removing the diffuser cartridge 24 from the vessel body 12. Furthermore, although the following discussion refers to diffuser cartridge 24, those skilled in the art will readily appreciate that the discussion equally applies to diffuser cartridge 124 and corresponding container 110.

According to one embodiment, the tool 34 is elongate and is formed from a plurality of separate tool elements, including a bottom element 36, and intermediate element 38, and a top element 40. The tool 34 is configured such that the tool 34 may be manually manipulated or held by an individual to insert or remove the diffuser cartridge 24 to or from the vessel body 12, with the tool 34 being configured to allow an individual's hand to remain outside of the vessel body 12 throughout the insertion or removal process. In this respect, the tool 34 and diffuser cartridge 24 collectively define a height $H_2$, which is larger than the height $H_1$ of the vessel body 12, which allows a portion of the tool to extend beyond the upper rim 21 of the vessel body 24 when the tool 34 is engaged with the diffuser cartridge 24, and with the diffuser cartridge 24 nested within the retaining cavity 32.

The bottom element 36 includes a first end portion 42 adapted to interface with the diffuser cartridge 24 and a second end portion 44 adapted to interface with the intermediate element 38. The first end portion 42 includes a cylindrical wall disposed about a cavity, with the cylindrical wall terminating at a distal end 46. The cavity is adapted to receive the diffuser cartridge 24, with the inner diameter of the cylindrical wall being slightly larger than the outer diameter of the diffuser cartridge 24. A pair of diametrically opposed cutouts 48 extend into the cylindrical wall from the distal end 46, with each cutout having an axial segment 50 and a radial segment 52. The axial segment 50 extends from the distal end 46 and the radial segment 52 is spaced from the distal end 46. The dimension of the cutouts 48 corresponds to a pair of diametrically opposed nubs or protrusions 54 formed on the diffuser cartridge 24. In particular, the cutouts 48 are configured such that each nub 54 may be received within a respective cutout 48 to operatively couple the bottom element 36 to the diffuser cartridge 24.

The second end portion 44 is connected to the first end portion 42 via an intermediate elongate segment 56, which has a smaller diameter than the cylindrical wall of the first end portion 42. The second end portion 44 includes a male connector wall 58 having an outer diameter smaller than the diameter of the intermediate elongate segment 56. A pair of diametrically opposed locking tabs 60 extend radially outward from the male connector wall 58. According to one embodiment, each locking tab 60 extends radially outward by a distance equal to one-half of the difference between the diameter of the intermediate elongate segment 56 and the diameter of the male connector wall 58.

The intermediate element 38 includes a first end portion 62 and a second end portion 64 and an intermediate segment 66 disposed therebetween. The first end portion 62 is adapted to interface with the bottom element 36 and the second end portion 64 is adapted to interface with the top element 40. In the exemplary embodiment, the first end portion 62 defines a female-type connector adapted to engage with the male-type connector of the bottom element 36, while the second end portion 64 defines a male-type connector adapted to engage with a female-type connector on the top element 40.

The first end portion 62 defines a cylindrical wall having a pair of diametrically opposed cutouts 68 extending into the cylindrical wall from a distal end 70. Each cutout 68 includes an axial segment and a radial segment. The cutouts 68 are sized and configured to enable the locking tabs 60 of the bottom element 36 to extend therein for coupling the bottom element 36 to the intermediate element 38.

The cylindrical wall of the first end portion 62 transitions to the intermediate segment 66, with the outer diameter of the cylindrical wall being the same as the outer diameter of the intermediate segment 66.

The second end portion 64 includes a male connector wall 72 having an outer diameter smaller than the diameter of the intermediate elongate segment 66. A pair of diametrically opposed locking tabs 74 extend radially outward from the male connector wall 72. According to one embodiment, each locking tab 74 extends radially outward by a distance equal to one-half of the difference between the diameter of the intermediate segment 66 and the diameter of the male connector wall 72.

The top element 40 includes a first end portion 76 and a second end portion 78. The first end portion 76 defines a cylindrical wall having a pair of diametrically opposed cutouts 80 extending into the cylindrical wall from a distal end 82. Each cutout 80 includes an axial segment and a radial segment. The cutouts 80 are sized and configured to enable the locking tabs 74 of the intermediate element 38 to extend therein for coupling the intermediate element 38 to the top element 40.

The cylindrical wall transitions into the second end portion 78, which includes an outwardly tapering wall to provide an ergonomically friendly gripping portion.

With the basic structure of the tool 34 described above, the following discussion will focus on an exemplary usage of the tool 34. To insert the diffuser cartridge 24 into the vessel body 12, a user would first assemble the tool 34 by connecting the first end portion 62 of the intermediate element 38 to the bottom element 36 and the second end portion 64 of the intermediate element 38 to the top element 40. Once the tool 34 is assembled, the user attaches the diffuser cartridge 24 to the tool 34 by aligning the cutouts 48 formed on the bottom element 36 with the nubs 54 formed on the diffuser cartridge 24. The user then advances the tool 34 over the cartridge 24, which causes the nubs 54 to pass through the axial segments 50 of the corresponding cutouts 48. The user then rotates the tool 34 a first direction to allow the nubs 54 to pass through the radial segments 52 of the corresponding cutouts 48. Once the nubs 54 pass through both the axial and radial segments 50, 54, the diffuser cartridge 24 is attached to the tool 34.

The diffuser cartridge 24 is then inserted into the vessel body 12 by holding the tool 34 at the top element 40 and aligning the diffuser cartridge 24 and bottom element 36 of the tool 34 with the opening of the vessel body 12. The user lowers the tool/cartridge assembly into the vessel body 12 until the diffuser cartridge 24 reaches the retaining wall 30.

When the diffuser cartridge 24 is aligned with the retaining wall 30, the user presses/pushes the tool 34 therein until the diffuser cartridge 24 is nested within the retaining cavity 32. Once the diffuser cartridge 24 is secured/nested within the retaining cavity 32, the user rotates the tool 34 in a second direction opposite to the first direction, which causes the nubs 54 to retreat back through the radial segments 52 of the cutouts 48 formed in the bottom element 36. The user then lifts the tool 34, which causes the nubs 54 to retreat through the axial segments 50, which ultimately allows the tool 34 to become disengaged from the diffuser cartridge 24. The tool 34 is then completely removed from the vessel body 12, and the user may continue using the vessel body 12 with the diffuser cartridge 24 secured therein.

To remove the diffuser cartridge 24, the user again assembles the tool 34, as described above, if the tool 34 is disassembled. The assembled tool 34 is then inserted into the vessel body 12 until the bottom element 36 reaches the diffuser cartridge 24. The user then rotates the tool 34 to align the cutouts 48 with the nubs 54. Once the nubs 54 are aligned, the user presses down to allow the nubs 54 to pass through the axial segment 50, and then rotates the tool 34 in the first direction to allow the nubs 54 to pass through the radial segment 52, and ultimately, secure the tool 34 to the diffuser cartridge 24. The user then holds the vessel body 12 in one hand, and pulls on the tool 34 to overcome the engagement force holding the diffuser cartridge 24 to the retaining wall 30, thereby releasing the diffuser cartridge 24 from the retaining wall 30. The user then pulls the tool/cartridge assembly from the vessel body 12 until the tool 34 and diffuser cartridge 24 are completely removed from the vessel body 12.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A tool system comprising:
    a fluid containment vessel having a base, a retaining wall coupled to the base, and an upper rim, the base and upper rim defining a vessel height;
    a diffuser cartridge being detachably engageable with the retaining wall to assume a nested configuration;
    a tool having:
    a bottom segment having:
        a first end portion having a cavity complementary in shape to the diffuser cartridge and adapted to receive a portion of the diffuser cartridge and be selectively engaged with the diffuser cartridge, the first end portion having:
            an end face;
            an inner surface and an outer surface, both of which extend from the end face;
            and a channel extending in a first direction from the end face and in a second direction from the inner surface toward the outer surface, the channel having an axial segment and a radial segment, the radial segment being spaced from the end face and including a first portion that is of a first width and a second portion that is of a second width greater than the first width, the first portion being positioned between the second portion and the axial segment and being formed by a convex surface spaced from the end face;

and a second end portion having a bottom segment connector;

an intermediate segment separate from the bottom segment and having:
  a first intermediate connector adapted to engage with the bottom segment connector;
  and a second intermediate connector;

a top segment separate from the bottom segment and intermediate segment, the top segment having:
  a top segment connector adapted to engage with the second intermediate connector;

at least one of the bottom segment, the intermediate segment, and the top segment including a slot formed therein;

and at least one of the bottom segment, the intermediate segment, and the top segment including a protrusion sized and configured to be extendable within the slot of another one of the bottom segment, the intermediate segment, and the top segment;

the intermediate segment being connected to the bottom segment and the top segment when the tool is in an assembled configuration, the tool being sized and configured such that an end surface of the diffuser cartridge and a portion of the top segment of the tool collectively define an operating length greater than the vessel height.

2. The tool system recited in claim 1, wherein the tool top segment includes an enlarged end portion opposite the top segment connector, the enlarged end portion being sized and configured to be grippable by a user.

3. The tool system recited in claim 1, wherein the tool is sized and configured to extend from the diffuser cartridge and beyond the upper rim of the fluid containment vessel when the first end portion is engaged with the diffuser cartridge.

4. The tool system recited in claim 1, wherein the tool bottom segment, the tool intermediate segment and the tool top segment are formed from a plastic material.

5. The tool system recited in claim 1, wherein the tool intermediate segment and portions of the tool top segment and the tool bottom segment each define an outer diameter substantially equal to each other.

6. The tool system recited in claim 1, wherein the channel extends in the second direction from the inner surface completely to the outer surface.

7. A tool system comprising:
a fluid containment vessel having a base and an upper rim defining a vessel height, and a retaining wall coupled to the base,
a diffuser cartridge detachably engageable with the retaining wall to assume a nested configuration,
a tool having:
  an elongate tool body having a first end portion adapted to be selectively engaged with the diffuser cartridge and a second end portion adapted to be grippable by a user, the first end portion having:
    an end face;
    an inner surface and an outer surface, both of which extend from the end face;
    and a channel extending in a first direction from the end face and in a second direction from the inner surface toward the outer surface, the channel having an axial segment and a radial segment, the radial segment being spaced from the end face and including a first portion that is of a first width and a second portion that is of a second width greater than the first width, the first portion being positioned between the second portion and the axial segment and being formed by a convex surface spaced from the end face;
    a cavity adapted to receive a portion of the diffuser cartridge when the first end portion of the bottom segment is engaged with the diffuser cartridge;
  the elongate tool body including a plurality of body segments cooperatively engageable with each other, a first one of the plurality of body segments includes a channel, and a second one of the plurality of body segments includes a protrusion configured to be received within the channel to engage the first one of the plurality of body segments to the second one of the plurality of body segments;
  the elongate tool body being sized and configured to extend from the diffuser cartridge and beyond the upper rim of the fluid containment vessel when the first end portion is engaged with the diffuser cartridge when the diffuser cartridge is in the nested configuration.

8. The tool system recited in claim 7, wherein the plurality of body segments are selectively transitional between a disengaged configuration, wherein the plurality of body segments are detached from each other, and an assembled configuration, wherein the plurality of body segments are interconnected to each other.

9. The tool system recited in claim 7, wherein adjacent ones of the plurality of body segments are adapted to become engaged with each other via relative rotation of one body segment relative to another body segment.

10. The tool system recited in claim 7 wherein the elongate tool body is formed of a plastic material.

11. The tool system recited in claim 7, wherein the channel extends in the second direction from the inner surface completely to the outer surface.

12. A tool system comprising:
a diffuser cartridge;
a bottle having a base, a month, and a retaining wall coupled to the base, the diffuser cartridge being detachably engageable with the retaining wall to assume a nested configuration, a length being defined as the distance extending from the top of the diffuser cartridge item when attached to the base, to the mouth of the bottle; and
an elongate tool body having a first end having a recess adapted to receive a portion of the diffuser cartridge when the first end is engaged with the diffuser cartridge, the first end having an end face, an inner surface, and an outer surface, both the inner and outer surfaces extending from the end face;
said elongate tool body having a channel extending from the end face and the inner surface, the channel being configured to receive a section of the diffuser cartridge, the channel including an axial segment and a radial segment, the radial segment including a first portion that is of a first width and a second portion that is of a second width greater than the first width, the first portion being positioned between wide second portion and the axial segment and being formed by a convex surface of the tool body spaced from the end face;
said elongate tool body have a second hand grip end;
and said elongate tool body having a length extending from the grip end to said first end that is greater than the length.

13. The tool system recited in claim 12, wherein the tool body includes a plurality of body segments cooperatively engageable with each other.

14. The tool system recited in claim 13, wherein the plurality of body segments are selectively transitional between a disengaged configuration, wherein the plurality of body segments are detached from each other, and an assembled configuration, wherein the plurality of body segments are interconnected to each other.

15. The tool system recited in claim 13, wherein adjacent ones of the plurality of body segments are adapted to become engaged with each other via relative rotation of one body segment relative to another body segment.

16. The tool system recited in claim 13, wherein a first one of the plurality of body segments includes a channel formed therein, and a second one of the plurality of body segments includes a protrusion adapted to be received within the channel to engage the first one of the plurality of body segments to the second one of the plurality of body segments.

17. The tool system recited in claim 16, wherein the protrusion and the channel are configured such that the protrusion is advanceable through the channel by relative translation and rotation of the first one and the second one of the plurality of body segments.

18. The tool system recited in claim 12, wherein said elongate tool body include a diameter which increases from an intermediate section toward the second hand grip end to define an enlarged portion of the elongate tool body being sized and configured to be grippable by a user.

19. The tool system recited in claim 12, wherein the channel extends from the inner surface to the outer surface.

* * * * *